United States Patent [19]

Lang et al.

[11] Patent Number: 4,581,937
[45] Date of Patent: Apr. 15, 1986

[54] METHOD OF SUPPRESSING UNWANTED INDICATIONS IN AUTOMATED ULTRASONIC TESTING

[75] Inventors: Raimund Lang, Alzenau; Dieter Lather, Rückersbach, both of Fed. Rep. of Germany

[73] Assignee: KTV-Systemtechnik GmbH, Fed. Rep. of Germany

[21] Appl. No.: 651,382

[22] Filed: Sep. 17, 1984

[30] Foreign Application Priority Data

Jun. 7, 1984 [DE] Fed. Rep. of Germany ....... 3421150

[51] Int. Cl.[4] ............................................ G01N 29/04
[52] U.S. Cl. ...................................... 73/611; 73/612; 73/613; 73/618; 73/598
[58] Field of Search ................. 73/602, 613, 598, 612, 73/611, 618

[56] References Cited

U.S. PATENT DOCUMENTS

| 3,346,068 | 10/1967 | Woods et al. | 73/613 |
| 4,187,725 | 2/1980 | Gavrev et al. | 73/613 |
| 4,205,553 | 6/1980 | Rudis et al. | 73/611 |
| 4,432,235 | 2/1984 | Renzel et al. | 73/611 |
| 4,518,811 | 8/1965 | Sternberg et al. | 73/611 |

OTHER PUBLICATIONS

*Ultrasonic Testing of Materials,* Krautkramer, Springer-Verlag, 1977, pp. 247-252.

Primary Examiner—Howard A. Birmiel
Attorney, Agent, or Firm—Seidel, Gonda, Goldhammer & Abbott

[57] ABSTRACT

The invention relates to a method of suppressing unwanted indications in automated ultrasonic testing of a test piece.

In order to improve the suppression of unwanted indications, in particular in the case of extended statistical suppression, a variable discriminator threshold (3) is derived from the highest of all maximum amplitudes (2) by means of a predetermined amplitude difference (4), wherein the ultrasonic signals are not evaluated as flaw signals when only said variable discriminator threshold (3) is exceeded but are evaluated as flaw signals only when additionally at least the highest of all maximum amplitudes (2) exceeds the fixed discriminator threshold (1) preset for the testing operation.

4 Claims, 1 Drawing Figure

METHOD OF SUPPRESSING UNWANTED INDICATIONS IN AUTOMATED ULTRASONIC TESTING

BACKGROUND OF THE INVENTION

The invention relates to a method of suppressing unwanted indications in ultrasonic testing in automated systems.

It has been known that it is possible in automated ultrasonic testing to distinguish unwanted indications over actual flaw indications by a plurality of techniques. Among the known methods are the following:

(a) Statistical Interference Suppression

By counting the amplitude-discriminated signals, which are above the so-called monitor thresholds or evaluation thresholds, in uninterrupted sequence and preselected numbers.

(b) Extended Statistical Interference Suppression

By counting the amplitude-discriminated signals, which are above a low evaluation threshold, in uninterrupted sequence and preselected numbers, while at the same time a higher evaluation threshold is exceeded at least once.

(c) Aerial-Type Suppression

By means of additional amplifiers, signals (normally spurious electrical signals) are picked up from the air via an aerial and are amplified. The amplified signals inhibit the so-called monitors provided for test evaluation in dependence on the propagation times typical for the ultrasonic amplifiers.

However, all of the above-mentioned techniques have drawbacks when, for instance, upon use of the statistical interference suppression (which requires that the monitor or evaluation threshold is exceeded during several test cycles in succession) or upon use of the extended statistical interference suppression (which requires that the fixed lower monitor threshold is exceeded during several test cycles in successsion and that the likewise fixed upper monitor threshold is exceeded in at least one test cycle) the flaw signal is either below the preset value of the number of successively required flaw signals or in the case of aerial-type suppression the necessary conditions are not met by electrical signals.

Indeed, in the case of extended statistical interference suppression there is a considerable limitation at relatively high amplitudes due to the lower discriminator threshold which is fixed prior to commencement of the test. In case of a fixed discriminator threshold the signal dynamics expected due to the test cannot be taken into account. The mentioned prior art is substantially described in German patent DE-PS 2,704,132.

It is the object of the present invention to provide a method of blanking unwanted indications, by which the deficiencies in prior art methods are eliminated and the ultrasonic testing becomes more reliable.

SUMMARY OF THE INVENTION

The invention is directed to a method of suppressing unwanted indications in automated ultrasonic testing in which a test piece and an associated ultrasonic scanning head are moved relative to one another at a predetermined speed, the peak amplitude values of the ultrasonic signals reflected from the interior of the test piece are detected and a statistical interference suppression analysis is performed on the detected signals. The invention comprises the steps of determining a maximum peak amplitude value for the reflected signals during a predetermined test interval, establishing for the test interval a variable threshold value which is less than the maximum peak amplitude value by a preselected amount, establishing a fixed threshold value representative of a flaw to be detected, comparing successive peak amplitude values of the detected signals to the variable and fixed threshold values, counting the number of successive peak amplitude values which exceed the variable threshold value, and generating a flaw signal only when the maximum peak amplitude value exceeds the fixed threshold value and the number of successive detected signals which exceed the variable threshold value are greater than or equal to a preselected number.

This method takes into account the dynamic nature of an error signal by deriving the variable threshold, or discriminator threshold, value which is used for the statistical interference suppression from the maximum peak amplitude of the detected signals. Thus, a single random noise signal will not generate an erroneous indication, even in a high noise environment. The upper limit of the variable discriminator threshold should be below the fixed threshold, since the fixed threshold characterizes an absolute error during the test procedure.

DESCRIPTION OF THE DRAWING

The single FIGURE shows the amplitude characteristic of a flaw signal.

The drawing schematically shows the amplitude characteristic of a flaw signal plotted above the testing time. The time $t_1$, $t_2$ etc. in the drawing result from the clock frequency preselected for the testing operation, and the amplitudes $A_1$, $A_2$ etc. result from the reflection characteristic of the flaw signal in conjunction with the relative speed of scanning head and test piece.

Figure 1:
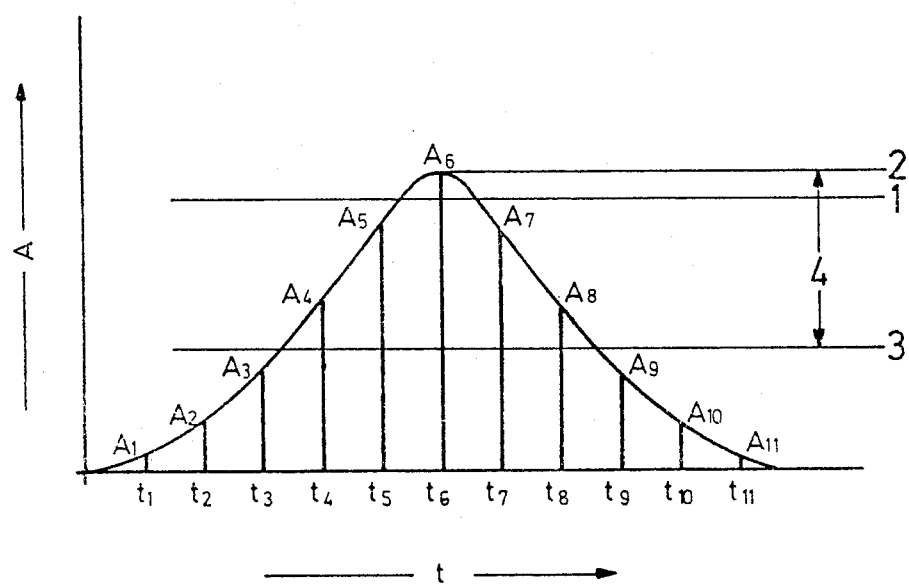

The envelope shown in the FIGURE shows a typical sequence of measured amplitude values during an ultrasonic testing or measuring procedure. The different amplitudes $A_1$ through $A_{11}$ are received at subsequent equal time periods within a test interval, which are controlled by a clock generator. It is believed that those skilled in the art of ultrasonic testing are thoroughly familiar with transmitting and receiving ultrasonic pulses at discrete, timed intervals within a test interval. Consequently, it is believed that this aspect of the invention need not be described in detail here.

The maximum peak amplitude is designated $A_6$, and is referred to by reference numeral 2. From this maximum peak amplitude 2 an amplitude difference, designated by reference numeral 4, is derived to define a variable discriminator threshold, designated by reference numeral 3. The difference 4 is chosen as required for the particular testing procedure.

Immediately below the maximum peak amplitude 2, a fixed amplitude threshold, designated by reference numeral 1, is set. Maximum peak amplitude $A_6$ is determined by a test run at the beginning of a testing procedure, for example using a sample test piece with a known flaw. Fixed threshold level 1 is set below maximum peak amplitude $A_6$ but above the range of variable discriminator threshold 3.

The envelope of the amplitudes $A_1$ to $A_{11}$ depends on the scanning head characteristic and on the characteristic of the flaw. The number of amplitudes within the envelope is a function of the preselected pulse repetition frequency and the relative speed of scanning head and test piece.

Moreover it is assumed in the example shown in the drawing that only the maximum amplitude $A_6$ (2) exceeds the discriminator threshold (1) of the evaluation means, which threshold is set for the final evaluation as an error.

For a reliable distinction between an unwanted indication and an ultrasonic flaw signal, the amplitudes detected before and after the signal $A_6$ (which is the signal with the highest amplitude within the sequence (2)) are examined as to how often they occur in uninterrupted sequence in excess of the amplitude $A_6$ minus a predetermined amplitude frequency (3). When the characteristic of the flaw amplitude is unchanged over a plurality of test cycles, the amplitudes $A_4$ to $A_8$ are selected as those amplitudes to which this fact applies. Thus, in the instant drawing five amplitude values in uninterrupted sequence would exceed the maximum amplitude of the sequence minus the predetermined amplitude difference (4).

For the blanking of unwanted indications, which in accordance with the definition occur sporadically and only once, statistical suppression is performed over the number of amplitudes which exceed the maximum amplitude minus a predetermined amplitude difference, i.e., a test is performed for multiple verification. The verification of a flaw will take place only when both conditions apply (discriminator threshold has been exceeded at least once, and multiple verification across the amplitude characteristic has been obtained).

The method of present invention may be summarized as follows. An ultrasonic scanner is moved past a test piece at a predetermined speed. The scanner detects ultrasonic signals reflected from the interior of the test piece. A test interval is defined equal to a predetermined number of detected signals, which may or may not represent scanning of the entire test piece. The peak amplitude of each detected signal is stored and the maximum peak amplitude is identified. The variable threshold 3 is set as a function of the maximum peak amplitude. The fixed threshold 1 is set as a function of the particular test procedure being performed. The maximum peak amplitude is compared to the fixed threshold and the entire sequence of detected signals in the test interval is compared to the variable threshold. The number of successive detected signals which exceed the variable threshold are counted. A flaw signal is generated if and only if the maximum peak amplitude exceeds the fixed threshold and the number of successive detected signals which exceed the variable threshold is greater than or equal to a preselected number.

We claim:

1. A method of suppressing unwanted indications in automated utlrasonic testing in which a test piece and an associated ultrasonic scanning head are moved relative to one another at a predetermined speed, the peak amplitude values of the ultrasonic signals reflected from the interior of the test piece are detected and a statistical interference suppression analysis is performed on the detected signals, comprising the steps of
  (a) determining a maximum peak amplitude value for the detected signals during a predetermined test interval,
  (b) establishing for the test interval a variable threshold value which is less than the maximum peak amplitude value by a preselected amount,
  (c) establishing a fixed threshold value independent of any peak amplitude value and representative of a flaw to be detected,
  (d) comparing successive peak amplitude values of the detected signals to the variable and fixed thresholds,
  (e) counting the number of peak amplitude values which exceed the variable threshold, and
  (f) generating a flaw signal only when the maximum peak amplitude value exceeds the fixed threshold value and the number of peak amplitude values which exceed the variable threshold value are greater than or equal to a preselected number.

2. The method according to claim 1, wherein the step of counting the number of peak amplitude values which exceed the variable threshold value is performed only when the maximum peak amplitude value exceeds the fixed threshold value.

3. The method according to claim 1, further comprising the step of storing in a memory peak amplitude values of detected signals which exceed the fixed threshold value while counting the number of peak amplitude values which exceed the variable threshold value and generating a flaw signal when the number of successive peak amplitude values which exceed the variable threshold value is greater than or equal to a preselected number.

4. The method according to claim 3, including the step of erasing the peak amplitude values which exceed the fixed threshold value from memory after a preselected time if the number of successive detected signals which exceed the variable threshold is less than the preselected number.

* * * * *